US006471721B1

(12) United States Patent
Dang

(10) Patent No.: US 6,471,721 B1
(45) Date of Patent: Oct. 29, 2002

(54) VASCULAR STENT HAVING INCREASED RADIOPACITY AND METHOD FOR MAKING SAME

(75) Inventor: Kenny Dang, San Jose, CA (US)

(73) Assignee: Advanced Cardiovascular Systems, Inc., Santa Clara, CA (US)

(*) Notice: Subject to any disclaimer, the term of this patent is extended or adjusted under 35 U.S.C. 154(b) by 0 days.

(21) Appl. No.: 09/475,380

(22) Filed: Dec. 30, 1999

(51) Int. Cl.⁷ .................................................. A61F 2/06
(52) U.S. Cl. .................... 623/1.34; 623/1.15; 623/1.44; 623/1.46
(58) Field of Search .............................. 623/1.15, 1.34, 623/1.42, 1.43, 1.46; 600/3

(56) References Cited

U.S. PATENT DOCUMENTS

| | | |
|---|---|---|
| 3,105,492 A | 10/1963 | Jeckel |
| 3,657,744 A | 4/1972 | Ersek |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,531,933 A | 7/1985 | Norton et al. |
| 4,553,545 A | 11/1985 | Maass et al. |
| 4,580,568 A | 4/1986 | Gianturco |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,681,110 A | 7/1987 | Wiktor |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,762,128 A | 8/1988 | Rosenbluth |

(List continued on next page.)

FOREIGN PATENT DOCUMENTS

| | | |
|---|---|---|
| EP | 0045627 | 2/1982 |
| EP | 0062300 A2 | 10/1982 |
| EP | 0221570 A2 | 5/1987 |
| EP | 0335341 B1 | 10/1989 |
| EP | 0338816 A2 | 10/1989 |
| EP | 0357003 A2 | 3/1990 |

(List continued on next page.)

OTHER PUBLICATIONS

Dotter, Charles T., Transluminally Placed Coilspring Endarterial Tube Grafts, *Investigative Radiology*, pp. 329–332, Sep./Oct. 1969.

Rösh, J., M.D., et al., Transjugular Intrahepatic Portacaval Shunt: An Experimental Work, *The American Journal of Surgery*, pp. 588–592, vol. 121, May 1971.

(List continued on next page.)

*Primary Examiner*—Corrine McDermott
*Assistant Examiner*—Alvin Stewart
(74) *Attorney, Agent, or Firm*—Fulwider Patton Lee & Utecht, LLP

(57) ABSTRACT

A stent for use in a patient's blood vessel to maintain the patency of the vessel contains strategically located radiopaque material. The strategic placement of the radiopaque material in the core structure of the stent functions to enhance the resolution of the stent under fluoroscopy. The initial part of the process includes forming a groove in a piece of tube stock and securing radiopaque material into the groove by press fitting or diffusion bonding. After the securing method, a layer of material can be sputtered coated over the only radiopaque material or over the entire stent. Finally, a pattern of struts and splines is cut into the tube composite to form the stent.

23 Claims, 2 Drawing Sheets

U.S. PATENT DOCUMENTS

| | | |
|---|---|---|
| 4,767,418 A | 8/1988 | Deininger et al. |
| 4,776,337 A | 10/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,922,905 A | 5/1990 | Strecker |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,041,126 A | 8/1991 | Gianturco |
| 5,059,211 A | 10/1991 | Stack et al. |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,135,536 A | 8/1992 | Hillstead |
| 5,158,548 A | 10/1992 | Lau et al. |
| 5,161,547 A | 11/1992 | Tower |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,195,984 A | 3/1993 | Schatz |
| 5,197,978 A | 3/1993 | Hess |
| 5,222,971 A | 6/1993 | Willard et al. |
| 5,226,913 A | 7/1993 | Pinchuk |
| 5,234,456 A | 8/1993 | Silvestrini |
| 5,242,452 A | 9/1993 | Inoue |
| 5,282,823 A | 2/1994 | Schwartz et al. |
| 5,282,824 A | 2/1994 | Gianturco |
| 5,290,305 A | 3/1994 | Inoue |
| 5,292,331 A | 3/1994 | Boneau |
| 5,304,200 A | 4/1994 | Spaulding |
| 5,314,444 A | 5/1994 | Gianturco |
| 5,314,472 A | 5/1994 | Fontaine |
| 5,330,500 A | 7/1994 | Song |
| 5,356,433 A | 10/1994 | Rowland et al. |
| 5,423,885 A | 6/1995 | Williams |
| 5,591,197 A * | 1/1997 | Orth et al. .................. 606/198 |
| 5,617,878 A | 4/1997 | Taheri |
| 5,733,326 A * | 3/1998 | Tomonto et al. ................ 623/1 |
| 5,824,042 A * | 10/1998 | Lomdardi et al. ............. 623/1 |
| 5,858,556 A * | 1/1999 | Eckert et al. ............... 428/586 |
| 5,938,697 A | 8/1999 | Killion et al. |
| 5,964,798 A * | 10/1999 | Imran ............................ 623/1 |
| 5,968,092 A * | 10/1999 | Buscemi et al. ........... 623/1.42 |
| 6,113,627 A * | 5/2000 | Jang ............................. 623/1 |
| 6,254,631 B1 * | 7/2001 | Thompsosn ................ 623/1.15 |
| 6,273,913 B1 * | 8/2001 | Wright et al. ............. 623/1.42 |
| 6,293,966 B1 * | 9/2001 | Frantzen .................... 623/1.15 |

FOREIGN PATENT DOCUMENTS

| | | |
|---|---|---|
| EP | 0361192 A3 | 4/1990 |
| EP | 0364787 A1 | 4/1990 |
| EP | 0372789 A3 | 6/1990 |
| EP | 0380668 B1 | 8/1990 |
| EP | 0407951 A2 | 1/1991 |
| EP | 0421729 A2 | 4/1991 |
| EP | 0423916 A1 | 4/1991 |
| EP | 0428479 B1 | 5/1991 |
| EP | 0517075 B1 | 12/1992 |
| EP | 0540290 B1 | 5/1993 |
| EP | 0541443 A1 | 5/1993 |
| FR | 2677872 | 12/1992 |
| GB | 2070490 A | 9/1981 |
| GB | 2135585 A | 9/1984 |
| JP | SHO58-501458 | 9/1983 |
| JP | 62 231657 | 10/1987 |
| JP | 62235496 A | 10/1987 |
| JP | SHO63-214264 | 9/1988 |
| JP | 01083685 A | 3/1989 |
| JP | 1-299550 | 12/1989 |
| JP | HEI02-174859 | 7/1990 |
| JP | HEI02-255157 | 10/1990 |
| JP | 3-9745 | 1/1991 |
| JP | 03009746 A | 1/1991 |
| JP | 3-151983 | 6/1991 |
| JP | HEI04-25755 | 2/1992 |
| WO | WO91/07139 | 5/1991 |
| WO | WO92/06734 | 4/1992 |
| WO | WO92/09246 | 6/1992 |
| WO | WO97/25937 | 7/1997 |
| WO | WO98/20927 | 5/1998 |
| WO | WO98/32412 | 7/1998 |
| WO | WO99/17680 | 4/1999 |
| WO | WO99/39661 | 8/1999 |

OTHER PUBLICATIONS

Dotter, Charles T., Transluminal Expandable Nitinol Coil Stent Grafting: Preliminary Report, *Radiology Journal*, pp. 259–260, Apr. 1983.

Cragg, et al., Non–Surgical Placement of Arterial Endoprostheses: A New Technique Using Nitinol Wire, *Radiology Journal*, pp. 261–263, Apr. 1983.

Maas, et al., Radiological Follow–Up of Transluminally Inserted Vascular Endoprostheses; An Experimental Study Using Expanding Spirals, *Radiology Journal*, pp. 659–663, 1984.

70th Scientific Assembly and Annual Meeting: Scientific Program, *Radiology*, Washington, DC: Nov. 25–30, 1084, Special Edition, vol. 153(P).

C. R. Bard, PE Plus Peripheral Balloon Dilatation Catheter, *C. R. Bard, Inc.*, Aug. 1985.

Wright, et al., Percutaneous Endovascular Stents: An Experimental Evaluation, *Radiology Journal*, pp. 69–72, 1985.

Palmaz, et al., Expandable Intraluminal Graft; A Preliminary Study, *Radiology Journal*, pp. 73–77, 1985.

Program: Day 2 (Nov. 18) The Radiological Society of North America, *Radiology*, 1985.

Charnsangavej, C., M.D., et al., Endovascular Stent for Use in Aortic Dissection: An in Vitro Experiment, *Radiology*, pp. 323–324, vol. 157, No. 2, Nov. 1985.

Wallace, Michael J., et al., Tracheobronchial Tree: Expandable Metallic Stents Used In Experimental and Clinical Applications (Work in Progress), *Radiology*, pp. 309–312, vol. 158, Feb. 1986.

72nd Scientific Assembly and Annual Meeting: RSNA Scientific Program, *Radiology*, Chicago: Nov. 30–Dec. 5, 1986, Special Edition vol. 161(P).

Duprat, et al., Flexible Balloon–Expanded Stent For Small Vessels, *Radiology Journal*, pp. 276–278, 1987.

Rösch, Josef, M.D., et al., Gianturco Expandable Stents in Experimental and Clinical Use, paper presented at The Twelfth Annual Course on "Diagnostic Angiography and Interventional Radiology" Mar. 23–26, 1987 (San Diego, California).

Rösch, Joseph, M.D., et al., Gianturco Expandable Wire Stents in The treatment of Superior Vena Cava Syndrome Recurring After Maximum–Tolerance Radiation, *Cancer*, pp. 1243–1246, vol. 60, Sep. 1987.

Yoshioka, Tetsuya, et a., Self–Expanding Endovascular Graft: An Experimental Study in Dogs, *American Journal of Roentgeriology*, pp. 673–676, vol. 151, Oct. 1988.

Yoshioka, et al., 'Developemnt and Clinical Application of Biliary Endoprostheses Using Expandable Metallic Stents, *Japan Radiological Society*, 1988, vol. 48, No. 9, pp. 1183–1185 (with translation).

Mirich, et al., "Percutaneously Placed Endovascular Grafts for Aortic Aneurysms: Feasibility Study", *Radiology*, 1989, Part 2, pp. 1033–1037.

Charnsangavej, Chuslip, M.D., et al. Stenosis of the Vena Cava: Preliminary Assessment of Treatment with Expandable Metallic Stents, *Radiology*, pp. 295–298, vol. 161, Nov. 1986.

Rösch, Josef, M.D., et al., Experimental Intrahepatic Portacaval Anastomosis: Use of Expandable Gianturco Stents, *Radiology*, pp. 481–485, vol. 162, No. 1987.

Rösch, Josef, M.D., et al., Modified Gianturco Expandable Wire Stents in Experimental and Clinical Use, *Annales de Radiologie*, pp. 100–103, vol. 31, No. 2, 1998.

Lawrence, David D., Jr. et al., Percutaneous Endovascular Graft: Experimental Evaluation, *Radiology*, pp. 357–360, vol. 163, May 1987.

Rösch, Josef, et al., Gianturco Expandable Stents in Experimental and Clinical Use, pp. 121–124. Twelfth Annual Course on "Diagnostic Angiography and Interventional Radiology" Mar. 23–26, 1987, San Diego, California.

* cited by examiner

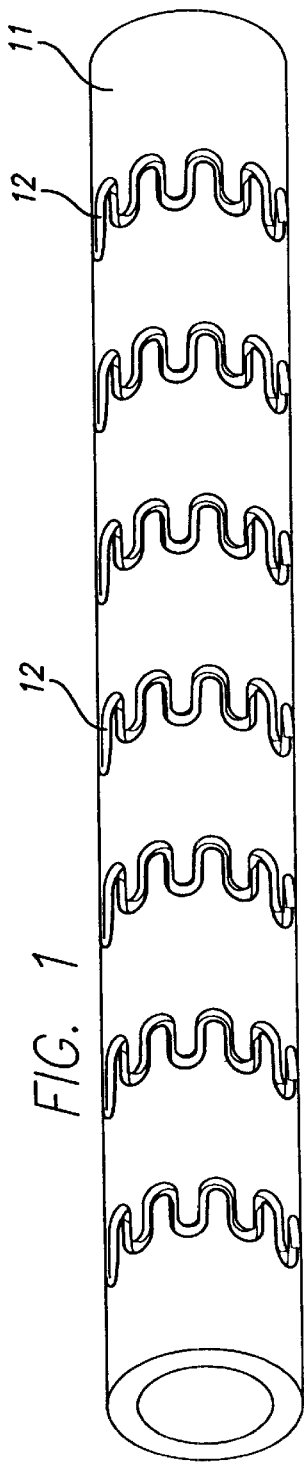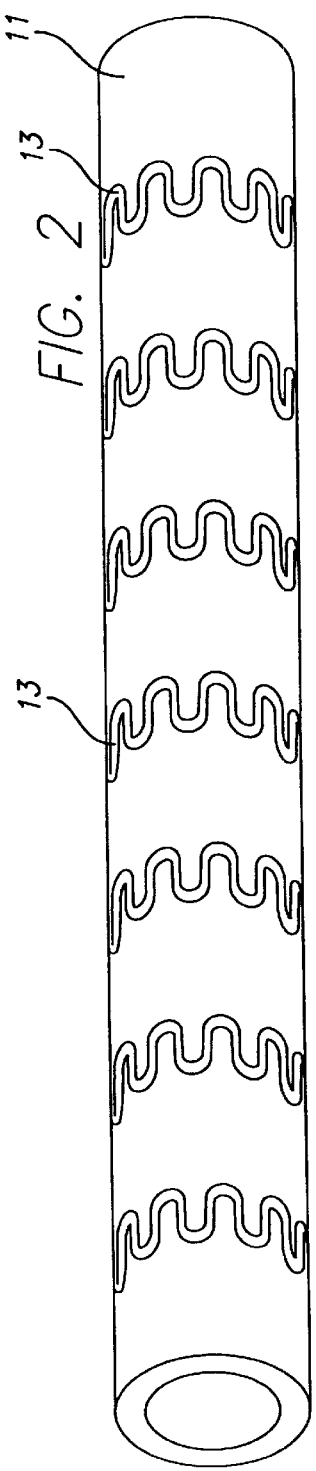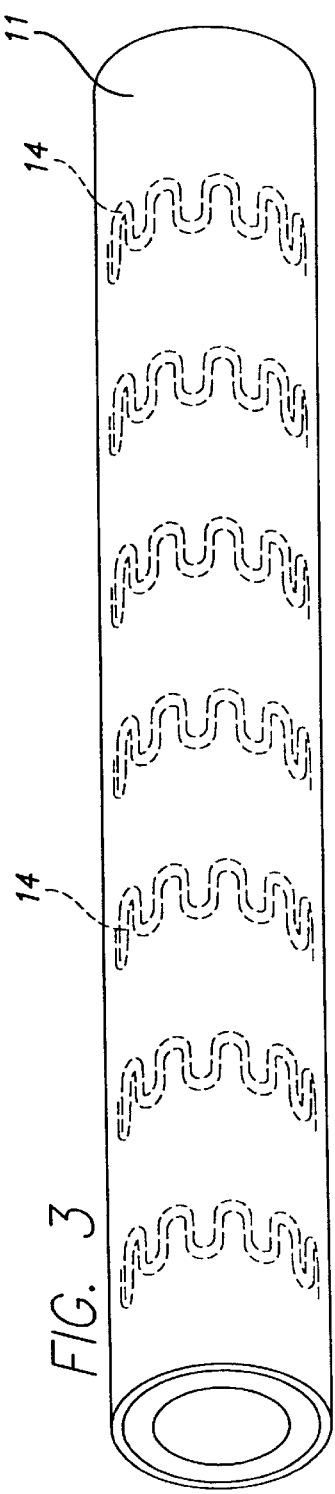

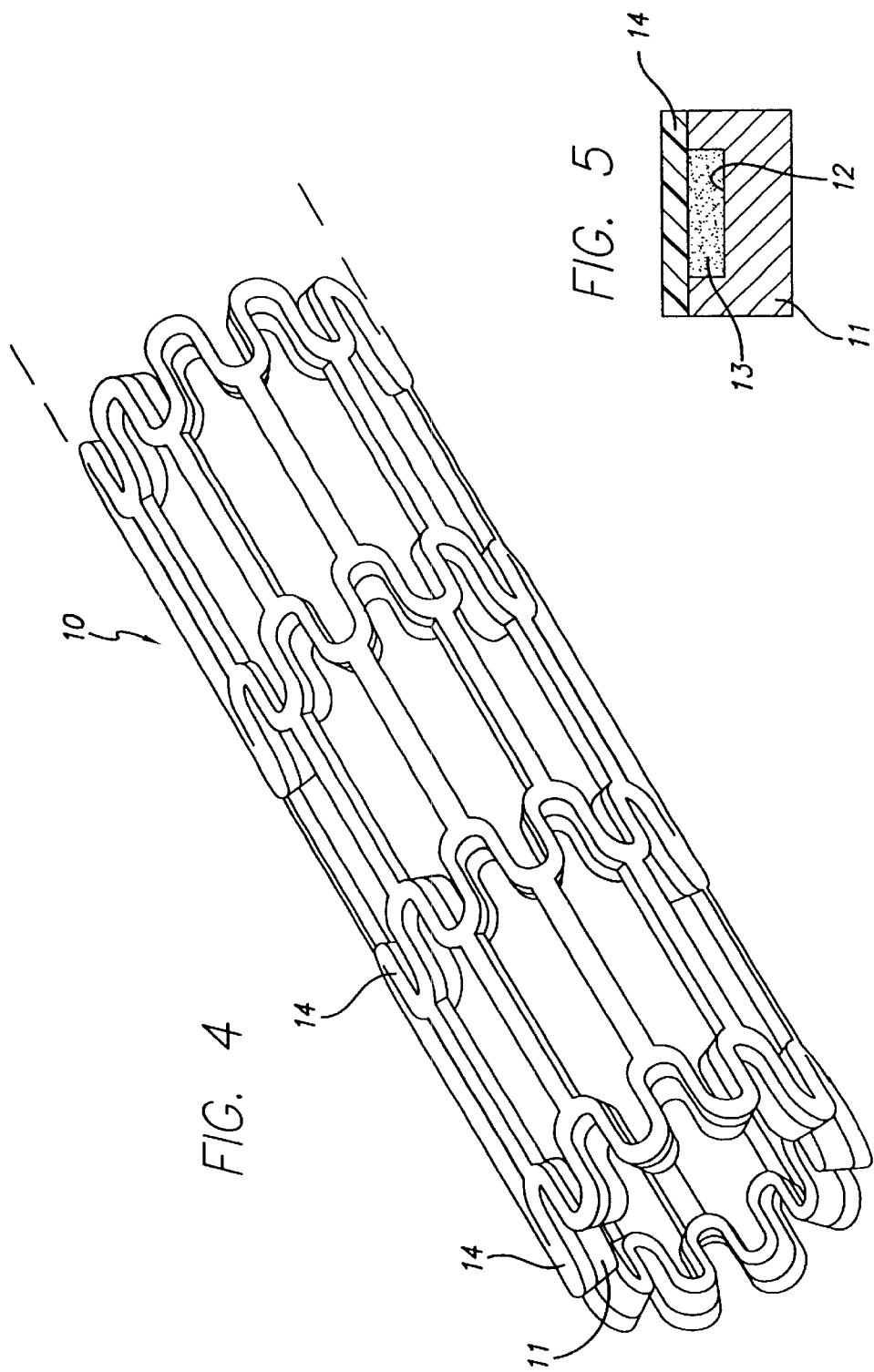

VASCULAR STENT HAVING INCREASED RADIOPACITY AND METHOD FOR MAKING SAME

BACKGROUND OF THE INVENTION

The present invention relates to improvements in increasing the radiopacity of stents and improvements in their method of manufacture, and, more particularly, to a stent and a method of manufacture where radiopaque material is secured to strategic location(s) on the stent to improve visibility of the stent under fluoroscopy.

Generally, stents are expandable endoprosthesis devices which are adapted to be implanted into a patient's body lumen to maintain the patency of the vessel. Stents are especially well-suited for the treatment of atherosclerotic stenosis in blood vessels. These devices are typically implanted into blood vessels by a delivery catheter which is inserted at an easily accessible location and then advanced through the patient's vasculature to the deployment site. The stent is initially maintained in a radially compressed or collapsed state to enable it to be maneuvered through the lumen. Once in position, the stent is usually deployed either automatically by the removal of a restraint, or actively by the inflation of an expandable member, such as balloon, about which the stent is mounted on the delivery catheter.

The stent must be able to satisfy a number of mechanical requirements. First, the stent must be capable of withstanding the structural loads that are imposed by the vessel walls. In addition to having adequate radial strength, the stent should be longitudinally flexible to allow it to be maneuvered through a vascular path and to enable it to conform to a deployment site which may not be linear or may flex. The stent material must allow the stent to undergo expansion which typically requires substantial deformation of localized portions of the stent's structure. Once expanded, the stent must maintain its size and shape throughout its service life despite the various forces that may come to bear thereon, including the cyclic loading induced by the beating heart. Finally, the stent must be biocompatible so as not to trigger any adverse vascular responses.

Fluoroscopy is typically used to facilitate the precise placement of a stent as well as to verify the position of a stent within the patient throughout the stent's service life. The use of radiopaque materials in the construction of the stent allows for its direct visualization. Accordingly, different patterns and contents of radioactivity have different effects on the direct visualization. For example, when a physician views a completely radiopaque stent under fluoroscopy, he/she will likely see an unclear and amorphous shape that extends outside the dimensions of the actual stent. The opposite will also be true where the stent possesses little radiopacity. In terms of fluoroscopic visibility, the optimal stent should be visible in a clear and detailed form without shape blurring. To date, no single material has been identified that simultaneously satisfies all requirements inherent in an optimal stent application. Those materials that do satisfy the mechanical requirements are either insufficiently or excessively radiopaque and/or are not adequately proven to be biocompatible in a vascular setting. Thus, simply constructing a stent which exhibits optimal radiopacity wholly out of a single material is not currently a viable option. A number of different approaches have, however, been employed wherein different materials are combined in an effort to render a mechanically sound and biocompatible stent to be visualized by a fluoroscope.

One procedure frequently used for accomplishing fluoroscopic visibility is through physical attachment of radiopaque markers to the stent. Conventional radiopaque markers, however, have a number of limitations. When attached to a stent, such markers may project from the surface of the stent, thereby exhibiting a departure from the ideal profile of the stent. Depending on their specific location, the marker may either project inwardly tending to disrupt blood flow or outwardly tending to traumatize the walls of the blood vessel. Additionally, when the metal used for the stent structure comes in contact with the metal used for the radiopaque marker, galvanic corrosion may occur. This corrosion may lead to separation of the metals and thereafter contamination of the blood stream with radiopaque material. Additionally, the radiopaque material may come into direct contact with living tissue which may be problematic, particularly if the material is not biocompatible.

Stents can also be marked by plating selected portions thereof with radiopaque material. A number of disadvantages with this approach are apparent. Because the radiopaque material comes into direct contact with living tissue, there can be a sizeable amount of tissue exposure. Additionally, when the stent is expanded and certain portions undergo substantial deformation, there is a risk that cracks will form in the plating which can separate from the underlying substrate. This side effect has the potential for creating jagged edges on the stent which may inflict trauma on the vessel wall or cause turbulence in the blood flow thereby inducing thrombogenesis. Moreover, once the underlying structural material becomes exposed, interfaces between the two disparate metals become subject to the same type of galvanic corrosion as mentioned above. Further, should the plating pattern cover less than all of the stent's surfaces, the margins between the plated and unplated regions are all subject to galvanic corrosion.

As a further alternative, a stent structure can be formed from a sandwich of structural and radiopaque materials. Tubes of suitable materials can be cold-drawn and heat treated to create a multi-layered tubing which can be cut into a stent. Struts and spines are formed in the multi layered tubing by cutting an appropriate pattern of voids into the tubing using well known techniques in the art. While this approach does provide a stent that has enhanced radiopacity and techniques fulfills necessary mechanical requirements, the thin cross section of the radiopaque material is usually exposed along the edges of all cut lines. The biocompatiblity of the radiopaque material remains an issue and more significantly, a sizeable area is created which is subject to galvanic corrosion. Any cuts in the sandwich structure cause two disparate metal interfaces, i.e. the juncture between the outer structural layer and the central radiopaque layer, as well the juncture between the central radiopaque layer and the inner structural layer, to become exposed to blood and tissue along the entire lengths of these cuts.

A stent configuration that overcomes the shortcomings inherent in previously known devices is therefore required. More specifically, a stent is needed that provides radiopaque properties enabling clear visibility under fluoroscopy and mechanical properties consistent for reliable and safe use.

A method of manufacturing the above mentioned stent configuration is also necessary. More specifically, a method is needed that combines the prerequisites of biocompatible materials and fluoroscopy into an advantageous method of manufacture.

SUMMARY OF INVENTION

The present invention provides a stent and method for manufacture which overcomes some of the shortcomings of previously known stents and methods of manufacturing stents. Most importantly, the stent has high resolution when viewed under fluoroscopy due to strategic placement of radiopaque material along the stent. The stent also fulfills the requirements of having sufficient flexibility, structural integrity and biocompatiblity, and being safe for deployment into a patient's vasculature.

Unique to the stent described herein is an advantageously selected pattern of radiopaque material formed on the stent. Compared to conventional stents, which are frequently obscured under fluoroscopy, the pattern of radiopaque material in the stent described herein leads to improved visibility under fluoroscopy. Unique to the process is a method of forming selected patterns of securely mounted radiopaque material on a stent substrate. Compared to some conventional processes of forming stents where radiopaque material is simply layered onto the stent structure, the process described herein utilizes a process of placing select patterns of grooves into the stent substrate. This grooving process allows precise placement and strong retention of radiopaque material into strategic locations of the stent.

The material employed for said underlying structure is selected for its structural and mechanical properties and may be the same general material used to make conventional stents. One preferred material is 316L stainless steel, although other materials such as nickel-titanium, cobalt based alloys, Nitinol and other types of stainless steel can be used. Such materials, when used in the 0.002" to 0.003" thickness, as is typical for stent applications, are often difficult to visualize fluoroscopically.

The grooving process is the first operation to be performed on a piece of tube stock. In this process, apattern of groove(s), preferably either rings or lines, is cut in the tube stock. The grooves should be strategically placed at targeted locations along the length of the tubing to obtain the desired radiopacity. The stent may employ one or a multiple number of grooves depending on radiopacity requirements. In forming the groove(s), an instrument, such as a conventional Swiss screw machine can be used. Alternative machines can also be used to perform the same grooving operation.

After the grooving process is performed on the tube stock, radiopaque material is inserted into the groove(s) by either press-fitting, diffusion bonding or laser bonding. One preferred radiopaque material is gold, although other radiopaque materials such as platinum, tantalum, iridium, or their alloys can also be used. When press-fit, the shapes of the strip(s) must be in close conformance with the shape of the groove(s) while being slightly larger than the size of the groove(s). The radiopaque strip(s) are combined with the groove(s) in the tube such that the difference in sizing causes the two metals to lock together in an interference fit. The interference fit insures a strong and long lasting bond between the two materials. When the radiopaque strip(s) are diffusion bonded, an entirely different process of attachment can be employed. In the diffusion bonding procedure, a vacuum is drawn and the entire assembly (tubing with radiopaque material inserted into the groove(s)) is heated to near the particular diffusion bonding temperature with the bonding surfaces still exposed to the vacuum environment. Thereafter, the bonding surfaces are brought into contact with very moderate pressure and maintained at a temperature and pressure sufficient for diffusion bonding. The assembly is then cooled, resulting in a substantially unitary diffusion bonded structure.

While not mandatory for this process, stainless steel can be applied over the radiopaque sections of the tube to promote biocompatibility and structural integrity. Additionally, the stainless steel coating can act to protect the radiopaque and structural materials from galvanically corroding. The stainless steel, preferably 316L can be applied by a sputtering procedure, a method of depositing a metallic film through the use of electric discharge. Sputter coating machines are commercially available and capable of applying an extremely even coating of material to a workpiece. The tubing may be rotated in front of a nozzle, the nozzle may be rotated about the tubing or a nozzle that completely surrounds the tubing may be employed to apply the sputter coating. While the preferred material for the sputtering is 316L stainless steel, other suitable material can be used also. Additionally, if a higher degree of structural rigidity is sought, the material can be sputtered across the entire length of the tube to a sufficient thickness such that the structural integrity of the stent is significantly increased.

After the tube has been processed as described above, a procedure for cutting the tube can be initiated. In this procedure, for example, the tubing is first placed in a rotatable fixture inside a cutting machine, where it is positioned relative to a laser. According to machine encoded instructions, the tubing is rotated and moved longitudinally relative to the laser. The laser selectively removes the material from the tubing by ablation and a pattern is cut into the tube. The laser cut provides a desired pattern of voids defining struts and spines which allows the stent to expand in an even manner, in accordance with well known and well established procedures. Thereafter, the stents are subjected to the standard industry practices of electro-polishing and possibly annealing. Another biocompatible outer layer could also be applied to the stent.

The above and other objects and advantages of this invention will be apparent from the following more detailed description when taken in conjunction with the accompanying drawings of exemplary embodiments.

BRIEF DESCRIPTION OF THE DRAWINGS

FIG. 1 is a perspective view of the tube stock with one particular pattern of grooves cut into the tube in a ring-shaped pattern, constant in diameter, and spaced apart longitudinally.

FIG. 2 is a perspective view of the tube stock with radiopaque material inserted into the grooves and annularly bonded in a complementary fit.

FIG. 3 is a perspective view of the tube stock with radiopaque material inserted into grooves with sputtered material entirely covering the markers.

FIG. 4 is a perspective view of a portion of a stent which can be cut from the composite tube stock illustrated in FIGS. 1–4 and embodying features of the present invention.

FIG. 5 is a cross sectional view of a representative strut of a stent made in accordance with the present invention.

DETAILED DESCRIPTION OF THE PREFERRED EMBODIMENTS

A radiopaque stent and the process of forming said stent is described herein. Unique to the stent is an advantageously selected pattern of radiopaque material which is affixed to the stent. Compared to conventional stents which are frequently obscured under flouroscopy, the pattern of radiopaque material in the stent of the present invention allows an easily discernable view of the stent under fluoroscopy. Unique to the process of manufacturing the stent is a method of forming selected patterns of radiopacity within the stent.

Compared to some conventional processes whereby radiopaque material is layered onto stent structures, the method of the present invention includes a grooving process which allows for precise location of radiopaque material into the core of the stent.

Referring now to the drawings, wherein like numerals indicate like elements, a representation stent 10 made in accordance with the present invention is shown in FIG. 4. The stent 10 can be made in any number of different strut patterns, depending on the particular application for the stent. The stent 10 is representative of just one design which can be used to form the various struts and spines. Referring now to FIG. 1, a piece of tube stock 11 to be used for the underlying structure of the stent is shown. The material employed for said underlying structure is selected for its structural and mechanical properties and may be the same material from which conventional stents are made. One preferred material is 316L stainless steel, although other materials such as nickel-titanium, cobalt based alloys, Nitinol and other types of stainless steel can be used. Such materials, when used in the 0.002" to 0.003" thickness which is typical for stent applications, are often difficult to properly visualize fluoroscopically.

As shown in FIG. 1, a series of grooves 12 may be formed in tube stock 11 by a Swiss screw machine operation, or other machinery. One preferred pattern of groove(s) is either ring(s) or line(s), but any other pattern can be used. Such grooves can be placed at targeted locations along the length of the tubing in order to obtain the desired radioactivity along the stent. In addition, the number of grooves can vary according to the stent's application. For instance, if high radiopacity is required, a plurality of grooves can be formed along the tube stock. If low radiopacity is required, as little as one groove can be formed along the tube stock. While one preferred machine to form the grooves is a conventional Swiss screw machine, other machines can be used to perform the same grooving operation.

Referring now to FIG. 2, the tube stock 11 may incorporate radiopaque material 13 inserted into the grooves 12. The radiopaque material can be formed into strips which are placed into the grooves. One preferred radiopaque material is gold, although other radiopaque materials such but not limited to, platinum, tantalum, iridium, or their alloys can also be used. The strips are preferably inserted into the grooves by either a press-fit, diffusion bonding or laser bonding. When the strips are press-fit into the grooves, their shape must be in close conformance with, but slightly larger than, the width of the groove. The press fit ensures an interference between the radiopaque strips and the tube material which secures both materials together in a strong, long-lasting bond. If the strips are diffusion bonded to the tube, a different type of process is necessary. First, a vacuum is drawn and the assembly, which includes the tube and radiopaque strips placed in the grooves, is heated to near diffusion bonding temperature with the bonding surfaces still exposed to the vacuum environment. Thereafter, the bonding surfaces are brought into contact with very moderate pressure and are maintained at a temperature and pressure sufficient for diffusion bonding. The assembly is then cooled, resulting in a substantially unitary diffusion bonded structure. The advantageously selected patterns of radiopacity will allow precise orientation or degree of expansion to be discerned by inspection of the fluoroscopic image when the stent is completed.

Referring now to FIG. 3, the tubing 11 may incorporate radiopaque material 13 in the form described above with the addition of a thin layer of stainless steel 14 covering the radiopaque material. The stainless steel is applied to the tubing by sputtering, a method of depositing a metallic film through the use of electric discharge. Sputter coating machines are commercially available and capable of applying an extremely even coating of material to a workpiece. In practice, the tubing may be rotated in front of a nozzle, the nozzle may be rotated about the tubing or a nozzle that completely surrounds the tubing may be employed to apply the sputter coating. While one preferred material for the sputtering is 316L stainless steel, other suitable material can be also be used. In addition to securing the radiopaque strip(s) to the tubing, the sputtered layer of metal can function to prevent galvanic corrosion and strengthen the entire stent. In this regard, the material can be sputtered to a sufficient thickness over selected regions of the tube 11 or over the entire tube such that the structural integrity of the stent is significantly increased.

Referring now to FIG. 4, the composite radiopaque tubing 11 is illustrated with a substantial amount of material removed to passing the struts and spines of the stent 10. In the material removal procedure, the tubing is placed in a rotatable fixture of a cutting machine where it is positioned relative to a laser. The machine rotates and moves the tubing longitudinally relative to the laser, in accordance with machine encoded instructions. The laser selectively removes the material from the tubing by ablation and a pattern 14 is cut into the tube. The laser cut provides a desired pattern of voids defining struts and spines while leaving both the radiopaque strips 13 and sputtered stainless steel coating 14 in strategic locations. The tube is therefore cut into the discrete pattern of the finished stent. Further details on how the tubing can be cut by a laser are found in U.S. Pat. Nos. 5,759,192 (Saunders) and 5,780,807 (Saunders), which have been assigned to Advanced Cardiovascular Systems, Inc. and are incorporated herein by reference in their entirely.

FIG. 4 illustrates a portion of a representative stent 10 where the radiopaque strips 13 and the sputtered coating 14 are integral to the stent 10 and accompany the cut patterns 14. FIG. 5 shows a cross sectional view of a representative strut of the stent 10 made in accordance with the present invention which has a strategically located radiopaque material and a sputtered coating 14 affixed thereto. In a preferred embodiment, the placement of the radiopaque material on the stock tubing can be coordinated with the particular pattern of struts and spines which will be cut into the tube to ensure that the radiopaque material is completely surrounded by the tubing material once the tube is cut. Therefore, there should be no edges on a strut or spine which exposes the layer of radiopaque material directly to blood or tissue. The layer of coating which is sputtered onto the radiopaque material should complete the encapsulation of the radiopaque material. In this manner, the layers of material should not be exposed to possible elements which can cause galvanic corrosion or the layers to delaminate. Thereafter the stent is subjected to the standard industry practices of electro-polishing and possibly annealing. A biocompatable outer layer could also be added to the stent surface.

It should be appreciated that the radiopaque material may not be completely surrounded by tubing material and the layer of sputter coating in all instances. It is possible that some radiopaque material may be exposed on the sides of the stent struts after the tubing is cut. However, exposure of the radiopaque material can be kept at a minimum to help prevent galvanic corrosion from occurring and the risk of cracks forming along the struts. It is still possible to sputter an additional layer of coating onto the stent after it has been cut to assure that no edges of the struts expose radiopaque material directly to blood and tissue. In this manner, the radiopaque material on the stent can be fully encapsulated. Alternatively, a stent manufactured in accordance with the present invention can be made by first placing the radiopaque material into the grooves formed on the tubing and then cutting the struts and spines of the stent prior to any coating of the tubing. Thereafter, once the struts and spines of the stent have been properly formed, the thin layer of coating could then be placed on the stent to fully encapsulate the radiopaque material.

An advantage of the stent, and the method for manufacture described above, lies in the resolution of the stent under fluoroscopy. As previously mentioned, the high resolution is due to the strategically placed radiopaque strips inserted into grooves formed in the stent. The benefits of the stent are immediately apparent in practice where a physician, who views the stent under fluoroscopy, will clearly see the size and location of the stent in the vessel of the patient. The clear view of the stent enables the physician to perform his function efficiently and safely without the worry of incorrectly approximating the size or location of the stent.

While a particular form of the invention has been illustrated and described, it will also be apparent to those skilled in the art that various modifications can be made without departing from the spirit and scope of the invention. More specifically, it should be clear that the present invention is not limited to tubular type stents nor is it limited to any particular method of forming the underlying stent structure. Additionally, the invention is not limited to the use of any particular materials in either the core, radiopaque coating or encapsulating layer nor is it intended to be limited to any particular coating or application method. Accordingly, it is not intended that the invention be limited except by the appended claims.

What is claimed is:

1. A method for forming a vascular stent having increased radiopacity, comprising:
    selecting a tube of structural material;
    forming at least one groove along the tube;
    inserting radiopaque material into the groove;
    securing said radiopaque material to the tube; and
    after the radiopaque material has been inserted into the groove, cutting the tube into a particular pattern to form the struts of a stent.

2. The method of claim 1, wherein:
    the tube of structural material is formed of a biocompatible material selected from the group consisting of stainless steel, nickel-titanium alloys, and cobalt based alloys.

3. The method of claim 1, wherein:
    the step of forming the groove comprises forming one continuous groove.

4. The method of claim 1, wherein:
    the radiopaque material is formed in a strip and the step of inserting the radiopaque material comprises inserting the strip into the groove.

5. The method of claim 4, wherein:
    the step of securing the strip includes press-fitting the strip into the groove.

6. The method of claim 4, wherein:
    the step of forming the groove comprises forming a plurality of grooves.

7. The method of claim 6, wherein:
    a plurality of strips of radiopaque material are inserted into the plurality of grooves.

8. The method of claim 1, wherein:
    the method of claim 1, wherein the step of securing the radiopaque material includes the step of laser binding the radiopaque material into the groove.

9. The method of claim 1, wherein:
    the step of securing the radiopaque material into the groove includes press-fitting the material into the groove.

10. The method of claim 1, wherein:
    the cutting step is performed by a laser.

11. The method of claim 1, wherein:
    the grooves are formed on the exterior of the tube.

12. The method of claim 1, wherein:
    the grooves are formed on the exterior of the tube in a selected pattern.

13. A method for forming a vascular stent having increased radiopacity, comprising:
    selecting a tube of structural material;
    forming at least one groove along the tube;
    inserting a strip of radiopaque material into the groove;
    securing said radiopaque material to the tube by diffusion bonding the strip of radiopaque material into the groove; and
    cutting the tube into a particular pattern to form the struts of a stent.

14. A method for forming a vascular stent having increased radiopacity, comprising:
    selecting a tube of structural material;
    forming at least one groove along the tube;
    inserting radiopaque material into the groove;
    securing said radiopaque material to the tube by diffusion bonding the radiopaque material into the groove; and
    cutting the tube into a particular pattern to form the struts of a stent.

15. A method for forming a vascular stent having increased radiopacity, comprising:
    selecting a tube of structural material;
    forming at least one groove formed as a plurality of rings along the tube;
    inserting radiopaque material into the groove;
    securing said radiopaque material to the tube; and
    cutting the tube into a particular pattern to form the struts of a stent.

16. A method for forming a vascular stent having increased radiopacity, comprising;
    selecting a tube of structural material;
    forming at least one groove along the tube;
    inserting radiopaque material into the groove;
    securing said radiopaque material to the tube;
    sputter coating a layer of metal over the exterior surface of the radiopaque material; and
    cutting the tube into a particular pattern to form the struts of a stent.

17. A method for forming a vascular stent having increased radiopacity, comprising:
    selecting a tube of structural material;
    forming at least one groove along exterior of the tube in a selected pattern;
    inserting radiopaque material into the groove;
    securing said radiopaque material to the tube; and
    cutting the tube into a particular pattern which forms the struts of a stent and selectively places radiopaque material on particular struts of the finished stent.

18. A stent having enhanced radiopacity, comprising:

a tubular section constructed of at least one segment of a tube, the tubular segment having at least one groove formed therein;

a radiopaque material fabricated in strips and disposed within the groove; and means for securing the material within the groove, wherein the means for securing the radiopaque material in the groove includes sputter coating a layer of over the radiopaque material.

19. A stent having enhanced radiopacity, comprising:

a tubular section constructed of at least one segment of a tube, the tubular segment having at least one groove formed therein;

a radiopaque material fabricated in strips and disposed within the groove; and means for securing the material within the groove, wherein the means for securing the radiopaque material within the groove includes diffusion bonding the material into the groove.

20. A stent having enhanced radiopacity, comprising:

a tubular section constructed of at least one segment of a tube, the tubular segment having a plurality of grooves formed therein;

a radiopaque material fabricated in strips and disposed within the grooves; and means for securing the material within the grooves, wherein the means for securing the radiopaque material within the grooves includes diffusion bonding the strips of radiopaque material into the grooves.

21. A stent having enhanced radiopacity, comprising:

a tubular section constructed of at least one segment of a tube, the tubular segment having a plurality of grooves formed therein;

a radiopaque material fabricated in strips and disposed within the grooves; and means for securing the material within the grooves, wherein the means for securing the radiopaque material in the grooves includes sputter coating a layer of metal over the strips of radiopaque material.

22. A method of fabricating a vascular stent having increased radiopacity, comprising:

selecting a tubing of biocompatible material;

forming a plurality of grooves circumferentially and longitudinally along the tubing;

placing radiopaque material into the grooves;

securing the radiopaque material within the grooves; and cutting the tube into a particular pattern to form the struts of a stent.

23. A method of fabricating a vascular stent having increased radiopacity, comprising:

selecting a tubing of biocompatible material;

forming a groove on the exterior of the tubing;

placing radiopaque material into the groove;

securing the radiopaque material within the groove; and cutting the tubing into a particular pattern to form a plurality of struts made entirely from the tubing and a plurality of composite struts having a first layer made from the material forming the tubing and a second layer of radiopaque material, the radiopaque material being selectively placed on struts to increase the overall radiopacity of the finished stent.

* * * * *

UNITED STATES PATENT AND TRADEMARK OFFICE
CERTIFICATE OF CORRECTION

PATENT NO. : 6,471,721 B1  Page 1 of 1
DATED : October 29, 2002
INVENTOR(S) : Kenny Dang It is certified that error appears in the above-identified patent and that said Letters Patent is hereby corrected as shown below:

Column 9,
Line 9, after "of", add -- metal --.

Signed and Sealed this

Eighteenth Day of February, 2003

JAMES E. ROGAN
*Director of the United States Patent and Trademark Office*